US006872713B1

United States Patent
Maes et al.

(10) Patent No.: US 6,872,713 B1
(45) Date of Patent: Mar. 29, 2005

(54) ANTIPROTOZOAL SAPONINS

(75) Inventors: Louis Jules Roger Marie Maes, Wechelderzande (BE); Nils Albert Gilbert Germonprez, Blankenberge (BE); Luc Emiel Mathilde Van Puyvelde, Waasmunster (BE); Norbert G. M. De Kimpe, Destelbergen (BE); Tran Ngoc Ninh, Hanoi (VN)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/868,755

(22) PCT Filed: Dec. 15, 1999

(86) PCT No.: PCT/EP99/10177

§ 371 (c)(1),
(2), (4) Date: Sep. 12, 2001

(87) PCT Pub. No.: WO00/38700

PCT Pub. Date: Jul. 6, 2000

(51) Int. Cl.$^7$ .......................... A61K 35/78; C07C 69/60; C07H 17/08
(52) U.S. Cl. ........................ 514/169; 514/169; 514/510; 514/515; 530/317; 530/318
(58) Field of Search ................................ 536/18, 9, 11; 514/198, 169; 424/180, 195.1

(56) References Cited

U.S. PATENT DOCUMENTS 5,064,823 A * 11/1991 Lee et al. .................... 514/198

5,922,837 A * 7/1999 Meinke et al. .............. 530/317

OTHER PUBLICATIONS

Apers, S. et al., "Separation of a triterpenoid saponin mixture from Maesa lanceolata: semipreparative reversed–phase wide pore high performance liquid chromatography with temperature control", *Journal of Pharmaceurical and Biomedical Analysis*, 1998, 18:4,5, 737–743.

El–On, J. et al., Topical Treatment of New and Old World cutaneous leishmaniasis in experimental animals, *Trans. Roy. Soc. Trop. Med. Hyg.*, 1987, 81, 734–737.

Sindambiwe, J. et al., "Evaluation of biological activity of triterpenoid saponins from Maesa lanceolata", *Journal of Natural Products*, May, 1998, 61:5, 585–590.

Sindambiwe, J. et al., "Triterpenoid saponins from Maesa Lanceolata", *Phytochemistry*, 1996, 41:1, 269–277.

* cited by examiner

*Primary Examiner*—Sabiha Qazi
(74) *Attorney, Agent, or Firm*—Woodcock Washburn LLP

(57) ABSTRACT

Saponins of formula (I), a stereoisomeric form thereof or a pharmaceutically acceptable addition salt thereof, wherein $R_1$ to $R_{12}$ have the meaning given in the description, can be isolated from plants of the family Myrsinaceae and used, to decrease the infectiousness of and reduce the mortality associated with protozoan parasites of the genus Leishmania which are responsible for a group of conditions known as leishmaniases.

4 Claims, No Drawings

ANTIPROTOZOAL SAPONINS

CROSS REFERENCE TO RELATED APPLICATIONS

This application is a National Stage application under 35 U.S.C. § 371 of PCT/EP99/10177 filed Dec. 15, 1999, which claims priority under 35 U.S.C. § 119 from EP 98204409.1, filed Dec. 22, 1998.

The present invention is concerned with a process for the isolation of antiprotozoal saponins from plants belonging to the family Myrsinaceae and the use of said saponins for preparing a medicament for treating hosts, both men and animals, infected by protozoan parasites of the genus Leishmania, and for alleviating clinical manifestations of, and curing disorders known as leishmaniases in said hosts.

Leishmaniases present a large variety of disease manifestations differing markedly in their severity and health impact. Primarily, leishmaniases are debilitating conditions caused by any of several species of Leishmania and are transmitted by several Phlebotomine sandflies. The leishmaniases appear to be far more abundant and of greater public health importance than has been previously recognized. Control of leishmanial infections is complicated because many species of sandfly are potential vectors, because many animal species can act as reservoir hosts and because diagnostic procedures (clinical, serological, parasitological) are not always applicable or have limited acceptable diagnostic value.

The manifestations may be visceral, mucocutaneous and/or cutaneous and the strain of the infecting organism and the immunologic status of the host can influence the clinical manifestations and outcome of the parasitic disease. Treatment of leishmaniases is complex and prolonged systemic treatment is imperative. The objectives of treatment are to cure the human or animal patient of an intracellular parasitic infection, to prevent relapse, to avoid development of unresponsiveness and to keep hospitalisation and overall treatment costs to a minimum. To achieve these objectives, appropriate drugs must be given at adequate dose levels and frequency for a suitable period of time. Despite the extensive research in the search of effective and well tolerated antileishmanial agents, only few agents have been discovered and are available to the patient. Currrently, two pentavalent antimony compounds that have to be administered by deep intramuscular injection are commonly used as first-line drugs: meglumine antimonate (Glucantim™, Farmitalia) and sodium stibogluconate (Pentostam™, Wellcome). Second-line drugs are amphothericin-B (in particular the liposomal formulations), pentamidine and allopurinol. The currently available therapies are not sufficiently effective and cause toxic side effects in the patient. In addition, their spectrum of activity is not sufficiently broad. For these reasons, the need for new medications remains very high. The present identification of new active principles will have use in the treatment of disorders caused by protozoan parasites belonging to the genus Leishmania.

Unexpectedly, triterpene saponins having very potent prophylactic as well as therapeutical activity against Leishmania have been isolated from the plants *Maesa balansae* and *M. lanceolata*, two species from the family Myrsinaceae, genus Maesa.

The invention is directed to a process for the isolation of triterpene saponins from plants belonging to the family Myrsinaceae, characterized in that said process comprises the steps of (a) removing apolar material from the dried plant parts with an apolar solvent, (b) extracting said plant parts with an alcohol, and (c) further purifying the saponins in the alcohol extract by liquid-liquid extraction, filtration and chromatography.

In particular, the apolar solvent is a halogenated hydrocarbon, e.g. dichloromethane or chloroform; and the alcohol is methanol, ethanol, isopropanol, butanol, each optionally admixed with water. Particularly useful is a mixture of methanol:water (90:10) or a mixture of ethanol:water (70:30) for isolating the fraction containing the saponins.

The saponins of the alcohol extract are further purified by (c1) evaporating the extract to dryness, (c2) partitioning the residue between butanol and water, (c3) evaporating the organic layer to dryness, (c4) washing the residue in a ketone and (c5) filtering off the crude saponin mixture.

In step (c2), the water layer is preferably extracted several times with n-butanol.

The invention is also directed to an alternative process for the isolation of triterpene saponins from plants belonging to the family Myrsinaceae, characterized in that said process comprises the steps of (a) extracting the dried plant parts with an alcohol and concentrating the extract, (b) removing the apolar fraction from the extract by liquid-liquid extraction with an apolar solvent, and (c) further purifying the saponins in the alcohol extract by liquid-liquid extraction, filtration and chromatography.

In particular, the alcohol is methanol, ethanol, isopropanol, butanol, each optionally admixed with water, preferably a mixture of ethanol:water (70:30); the apolar solvent is a hydrocarbon, e.g. hexane.

The saponins of the alcohol extract are further purified by (c6) extracting the aqueous fraction with butanol satured with water, (c7) evaporating the organic layer to dryness, (c8) washing the residue in a ketone, and (c9) filtering off the crude saponin mixture,:

In step (c6), the water layer is preferably extracted several times with n-butanol.

When the saponins are isolated from the plant genus Maesa, the chromatography can comprise reversed-phase liquid chromatography with gradient eluent system using A: 0.5% ammonium acetate in water B: methanol C: acetonitrile wherein at t=0, (A:B:C)=(60:20:20) and t=end, (A:B:C)=(0:50:50), or straight-phase liquid chromatography on silicagel.

These processes yield a mixture that consists essentially of saponins. In many pharmacological experiments described in the experimental part, this mixture of saponins was used. For the purpose of structure elucidation, this mixture was separated into the individual constituents by HPLC as described in the experimental part.

The present invention thus also relates to one or more triterpene saponins obtainable by the processes described herein, whether as a mixture or as isolated products.

In particular, the invention concerns triterpene saponins; obtainable from the plant genus Maesa, by chromatography comprising reversed-phase liquid chromatography with gradient eluent system using A: 0.5% ammonium acetate in water B: methanol C: acetonitrile wherein at t=0, (A:B:C) (60:20:20) and t=end, (A:B:C)= (0:50:50), and wherein said saponin has the following characteristics:

| | |
|---|---|
| Compound 1: | MW = 1532, $\lambda_{max}$ = 228.6 nm, $\lambda_{max2}$ = 273.3 nm; $t_R$ = 8.97 |
| Compound 2: | MW = 1510, $\lambda_{max}$ = 223.9 nm, $\lambda_{max2}$ = 274.5 nm; $t_R$ = 9.39 |
| Compound 3: | MW = 1532, $\lambda_{max}$ = 279.2 nm, $\lambda_{max2}$ = 223.9 nm; $t_R$ = 9.68 |
| Compound 4: | MW = 1510, $\lambda_{max}$ = 280.4 nm, $\lambda_{max2}$ = 222.7 nm; $t_R$ = 10.09 |
| Compound 5: | MW = 1574, $\lambda_{max}$ = 276.8 nm, $\lambda_{max2}$ = 225.0 nm; $t_R$ = 10.87; and |
| Compound 6: | MW = 1552, $\lambda_{max}$ = 279.2 nm, $\lambda_{max2}$ = 223.9 nm; $t_R$ = 11.37. |

The relative retention time $t_R$ is the mean value of 10 measurements versus the retention time of uracil on a column Hypersil BDS C-18, 3 µm, 100×4 mm.

Specifically, the present invention concerns triterpene saponins having the formula

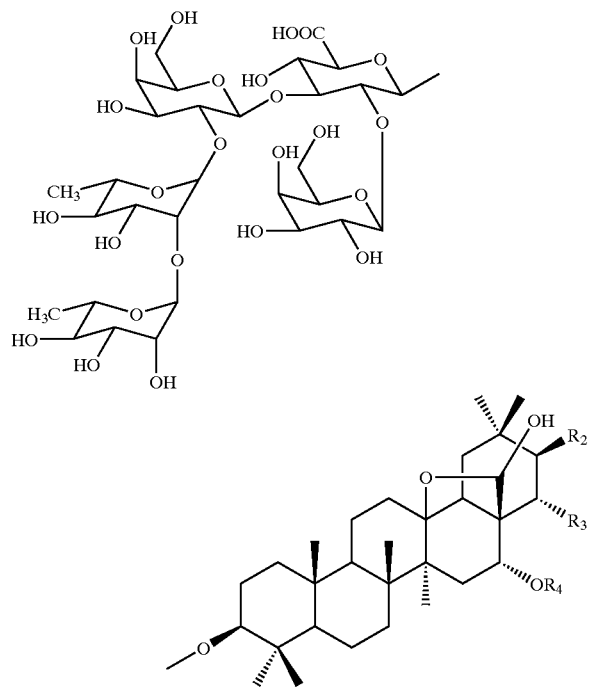

wherein $R_2$ is —O(C=O)$C_6H_5$ or —O(C=O)C(CH$_3$)=CHCH$_3$, $R_3$ is (E) or (Z) —O(C=O)CH=CH—$C_6H_5$, and $R_4$ is hydrogen or —(C=O)CH$_3$;

more in particular, in compound 1, $R_2$ is —O(C=O)$C_6H_5$,
 $R_3$ is (Z) —O(C=O)CH=CH—$C_6H_5$,
 $R_4$ is hydrogen;

in compound 2, $R_2$ is —O(C=O)C(CH$_3$)=CHCH$_3$,
 $R_3$ is (Z) —O(C=O)CH=CH—$C_6H_5$,
 $R_4$ is hydrogen;

in compound 3, $R_2$ is —O(C=O)$C_6H_5$,
 $R_3$ is (E) —O(C=O)CH=CH—$C_6H_5$,
 $R_4$ is hydrogen;

in compound 4, $R_2$ is —O(C=O)C(CH$_3$)=CHCH$_3$,
 $R_3$ is (E) —O(C=O)CH=CH—$C_6H_5$,
 $R_4$ is hydrogen;

in compound 5, $R_2$ is —O(C=O)$C_6H_5$,
 $R_3$ is (E) —O(C=O)CH=CH—$C_6H_5$,
 $R_4$ is —(C=O)CH$_3$;

in compound 6, $R_2$ is —O(C=O)C(CH$_3$)=CHCH$_3$,
 $R_3$ is (E) —O(C=O)CH=CH—$C_6H_5$,
 $R_4$ is —(C=O)CH$_3$;

Preferred compounds for use in the pharmaceutical compositions and methods of treatment of the present invention are compounds 3 and 4, in partcular compound 3.

Specifically, the present invention concerns the use of one or more triterpene saponins for the preparation of a pharmaceutical composition for treating leishmaniases in hosts infected by Leishmania species, characterized in that the saponin has the formula (I).

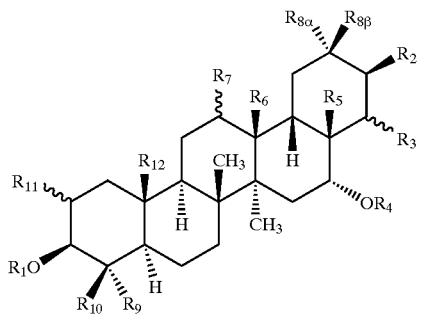

a stereoisomeric form thereof or a pharmaceutically acceptable addition salt thereof, wherein $R^1$ is hydrogen, —(C=O)$C_{1-5}$alkyl, —(C=O)$C_{2-5}$alkenyl, —(C=O)$C_{2-5}$alkenyl substituted with phenyl, a monosaccharide group or an oligosaccharide group;

$R_2$ is hydrogen, hydroxy, —O(C=O)$C_{1-5}$alkyl, —O(C=O)$C_{2-5}$alkenyl, —O(C=O)$C_6H_5$, or —O(C=O)$C_{2-5}$alkenyl substituted with phenyl, $R_3$ is hydrogen, hydroxy, —O(C=O)$C_{1-5}$alkyl, —O(C=O)$C_{2-5}$alkenyl, —O(C=O)$C_6H_5$, or —O(C=O)$C_{2-5}$alkenyl substituted with phenyl;

$R_4$ is hydrogen, $C_{1-6}$alkyl, —(C=O)$C_{1-5}$alkyl, —(C=O)$C_{2-5}$alkenyl, —(C=O)$C_6H_5$, or —(C=O)$C_{2-5}$alkenyl substituted with phenyl;

$R_5$ is CH$_3$, CH$_2$OH, CH$_2$OCH$_3$, CH$_2$O—C(=O)CH$_3$, CHO, COOH; or $R_5$ and $R_2$ form a divalent radical of formula —C(=O)—O—;

$R_6$ and $R_7$ are hydrogen; or taken together they form a bond; or $R_5$ and $R_6$ form a divalent radical of formula
 —CH$_2$—O— (a),
 —CH(OR$_{13}$)—O— (b),
 —C(=O)—O— (c),
 wherein $R_{13}$ is hydrogen, $C_{1-6}$alkyl or —(C=O)$C_{1-5}$alkyl $R_{8\alpha}$ and $R_{8\beta}$ each independently represent CH$_3$, CH$_2$OH, CH$_2$OCH$_3$, CH$_2$O—C(=O) $C_{1-5}$alkyl, CHO, CH(OCH$_3$)$_2$, CH=NOH, COOH; or $R_{8\beta}$ and $R_3$ form a divalent radical of formula —C(=O)—O—; or $R_{8\beta}$ and $R_5$ form a divalent radical of formula —$CH_2O$—CHOH—;

$R_9$ is $CH_3$, $CH_2OH$, $CH_2OCH_3$, $CH_2O$—$C(=O)C_{1-5}$alkyl, CHO, COOH;

$R_{10}$ is $CH_3$, $CH_2OH$, $CH_2OCH_3$, $CH_2O$—$C(=O)C_{1-5}$alkyl, CHO, COOH;

$R_{11}$ is hydrogen, hydroxy or O—$C(=O)C_{1-5}$alkyl; or $R_{10}$ and $R_{11}$ form a divalent radical of formula —$CH_2O$—; and $R_{12}$ is $CH_3$, $CH_2OH$, $CH_2OCH_3$, $CH_2O$—$C(=O)CH_3$, CHO, CH=NOH or COOH.

Preferred are the compounds of formula (I) wherein $R_1$ is hydrogen, —$(C=O)C_{1-5}$alkyl, or an oligosaccharide group;

$R_3$ is hydrogen, hydroxy, —$O(C=O)C_{1-5}$alkyl, —$O(C=O)C_{2-5}$alkenyl, —$O(C=O)C_{2-5}$alkenyl substituted with phenyl;

$R_4$ is hydrogen, $C_{1-6}$alkyl, —$(C=O)C_{1-5}$alkyl, —$(C=O)$ $C_{2-5}$alkenyl;

$R_5$ is $CH_2OH$, $CH_2O$—$C(=O)CH_3$, CHO; and $R_6$ and $R_7$ taken together form a bond; or $R_5$ and $R_6$ form a divalent radical of formula
—$CH_2$—O— (a),
—$CH(OR_{13})$—O— (b),
—$C(=O)$—O— (c),
wherein $R_{13}$ is hydrogen, $C_{1-6}$alkyl or —$(C=O)C_{1-5}$alkyl; and $R_7$ is hydrogen;

$R_{8\alpha}$ represents $CH_3$;

$R_{8\beta}$ represents $CH_3$, $CH_2OH$, CHO, CH(OCH3)$_2$, CH=NOH, COOH; or $R_{8\beta}$ and $R_3$ form a divalent radical of formula —$C(=O)$—O—; or $R_{8\beta}$ and $R_5$ form a divalent radical of formula —$CH_2O$—CHOH—;

$R_{10}$ is $CH_3$, $CH_2OH$;

$R_{11}$ is hydrogen, hydroxy or O—$C(=O)C_{1-5}$alkyl; or $R_{10}$ and $R_{11}$ form a divalent radical of formula —$CH_2O$—; and $R_{12}$ is $CH_3$, $CH_2OH$, $CH_2O$—$C(=O)CH_3$, CHO, CH=NOH.

Especially preferred compounds are those of formula (I) wherein $R_1$ is hydrogen or an oligosaccharide group;

$R_2$ is hydrogen, hydroxy, —$O(C=O)C_{1-5}$alkyl, —$O(C=O)C_{2-5}$alkenyl, —$O(C=O)C_6H_5$ or —$O(C=O)C_{2-5}$alkenyl substituted with phenyl;

$R_3$ is hydrogen, hydroxy, —$O(C=O)C_{1-5}$alkyl, —$O(C=O)C_{2-5}$alkenyl, —$O(C=O)C_{2-5}$alkenyl substituted with phenyl $R_4$ is hydrogen, $C_{1-6}$alkyl, —$(C=Q)C_{1-5}$alkyl, —$(C=O)$ $C_{2-5}$alkenyl, —$(C=O)C_{2-5}$alkenyl substituted with phenyl $R_5$ is $CH_2OH$, $CH_2OCH_3$, $CH_2O$—$C(=O)CH_3$, CHO, COOH; and $R_6$ and $R_7$ taken together form a bond; or $R_5$ and $R_6$ form a divalent radical of formula
—$CH_2$—O— (a),
—$CH(OR_{13})$—O— (b),
—$C(=O)$—O— (c),
wherein $R_{13}$ is hydrogen; and $R_7$ is hydrogen;

$R_{8\alpha}$ and $R_{8\beta}$ both represent $CH_3$;

$R_9$ is $CH_3$;

$R_{10}$ is $CH_3$;

$R_{11}$ is hydrogen; and $R_{12}$ is $CH_3$.

The compounds of formula (I) may be converted into each other through art-known processes. Particularly interesting processes are saponification in basic media, transesterification in acidic media, and enzymatic degradation of the oligosaccharide moiety so as to produce aglycones, i.e. compounds of formula (I) wherein $R_1$ is hydrogen.

The present invention also concerns a method of alleviating clinical manifestations of, and curing disorders known as leishmaniases attributable to infection by protozoan parasites of the genus Leishmania in both men and animals, comprising administering to an infected host a therapeutically effective amount of a compound of formula (I)

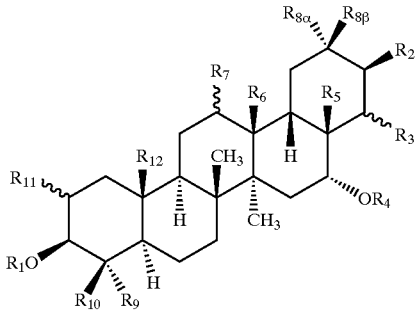

a stereoisomeric form thereof or a pharmaceutically acceptable addition salt thereof, wherein $R_1$ is hydrogen, —$(C=O)C_{1-5}$alkyl, —$(C=O)C_{2-5}$alkenyl; —$(C=O)C_{2-5}$alkenyl substituited with phenyl, a monosaccharide group or an oligosaccharide group;

$R_2$ is hydrogen, hydroxy, —$O(C=O)C_{1-5}$alkyl, —$O(C=O)C_{2-5}$alkenyl, —$O(C=O)C_6H_5$, or —$O(C=O)C_{2-5}$alkenyl substituted with phenyl;

$R_3$ is hydrogen, hydroxy, —$O(C=O)C_{1-5}$alkyl, —$O(C=O)C_{2-5}$alkenyl, —$O(C=O)C_6H_5$, or —$O(C=O)C_{2-5}$alkenyl substituted with phenyl;

$R_4$ is hydrogen, $C_{1-6}$alkyl, —$(C=O)C_{1-5}$alkyl, —$(C=O)$ $C_{2-5}$alkenyl, —$(C=O)C_6H_5$, or —$(C=O)C_{2-5}$alkenyl substituted with phenyl;

$R_5$ is $CH_3$, $CH_2OH$, $CH_2OCH_3$, $CH_2O$—$C(=O)CH_3$, CHO, COOH ; or $R_5$ and $R_2$ form a divalent radical of formula —$C(=O)$—O—;

$R_6$ and $R_7$ are hydrogen; or taken together they form a bond; or $R_5$ and $R_6$ form a divalent radical of formula
—$CH_2$—O— (a),
—$CH(OR_{13})$—O— (b),
wherein $R_{13}$ is hydrogen, $C_{1-6}$alkyl or —$(C=O)C_{1-5}$alkyl;

$R_{8\alpha}$ and $R_{8\beta}$ each independently represent $CH_3$, $CH_2OH$, $CH_2OCH_3$, $CH_2O$—$C(=O)$ $C_{1-5}$alkyl, CHO, CH(OCH$_3$)$_2$, CH=NOH, COOH;

$R_{8\beta}$ and $R_3$ form a divalent radical of formula —$C(=O)$—O—;

$R_{8\beta}$ and $R_5$ form a divalent radical of formula —$CH_2O$—CHOH—;

$R_9$ is $CH_3$, $CH_2OH$, $CH_2OCH_3$, $CH_2O\text{—}C(=O)C_{1-5}\text{alkyl}$, CHO, COOH;

$R_{10}$ is $CH_3$, $CH_2OH$, $CH_2OCH_3$, $CH_2O\text{—}C(=O)C_{1-5}\text{alkyl}$, CHO, COOH;

$R_{11}$ is hydrogen, hydrogen or $O\text{—}C(=O)C_{1-5}\text{alkyl}$; or $R_{10}$ and $R_{11}$ form a divalent radical of formula —$CH_2O$—; and $R_{12}$ is $CH_3$, $CH_2OH$, $CH_2OCH_3$, $CH_2O\text{—}C(=O)CH_3$, CHO, CH=NOH, or COOH.

For the purposes of treating leishmaniases, the compounds of formula (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injection, intravenous, intramuscular, intrasternal injection, intraarticular injection, or infusion techniques in subjects susceptible to leishmania organism infection.

The pharmaceutical compositions containing the active ingredient may be in a form suitable for oral use, for example, as tablets, troches, lozenges,:aqueous or oily solutions or suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets including but not limited to inert diluents, granulating and disintegrating agents, and lubricating agents. Tablets may be uncoated or they may be coated by known techniques to delay disintegration and adsorption in the gastrointestinal tract thereby providing a sustained action over a longer period; to mask an unpleasant taste or mouthfeel; or to improve appearance and recognizability.

Aqueous suspensions contain the active materials in admixture with excipients suitable for the manufacture of aqueous suspensions. Such excipients are suspending agents, dispersing or wetting agents. The said aqueous suspensions may also contain one or more preservatives, and oily suspensions may be formulated by suspending the active ingredient in a suitable vegetable oil or in a mineral oil such as liquid paraffin. The oily suspensions may contain thickening agents, sweetening agents, and flavoring agents to provide a palatable oral preparation. These compositions may be preserved by the addition of an acceptable antioxidant.

Dispersible powders and granules suitable for preparation of aqueous suspensions by the addition of water provide the active ingredient in admixture with a dispersing or wetting agent, suspending agent and one or more preservatives.

The pharmaceutical compositions of the present invention may, also be in the form of oil-in-water (o/w) or water-in-oil (w/o) emulsions. The oily phase may be a pharmaceutically suitable vegetable oil, arachis oils, or a mineral oil, containing suitable emulsifying agents and antioxidants. The aqueous phase may contain emulsifying agents, thickening agents and preservatives. The emulsions may also; contain sweetening, coloring and flavoring agents.

Syrups and elixirs may be formulated with sweetening agents. Such formulations may also contain a demulcent, a preservative and flavoring and coloring agents.

The pharmaceutical compositions may be in the form of a sterile injectable preparation, for example as a sterile injectable aqueous or oleaginous solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides, fatty-acids and other suitable additives of injectables. Suspensions may be formulated according to the known art using suitable dispersing or wetting agents and suspending agents.

The compounds of formula (I) may also be administered in the form of suppositories or other formulations such as solutions or suspensions for rectal administration of the drug. Suppositories can be prepared by mixing the drug with a suitable non-iritating excipient which is solid at ordinary temperatures but liquid at the rectal temperature to release the drug.

The daily dosage of the compounds of formula (I) may be varied over a wide range, e.g. from 1.0 to 2,000 mg. Preferably, the compound of formula (I) with a carrier in a pharmaceutical composition, is administered in subdivided doses containing 5, 10, 25, 50, 100, 150, 250 or 500 mg of the active ingredient for the appropriate dosage to the patient to be treated. An effective amount of the drug is ordinarily supplied at a dosage level of from about 0.01 mg to about 50 mg/kg of body weight. Preferably, the range is from about 0.1 mg to about 7 mg/kg of body weight.

It will be understood, however, that the specific dose level for any particular patient will depend upon a variety of factors including the activity of the specific compound employed, the age, body weight, general health, sex, diet, time of administration, route of administration, rate of excretion, drug combination and the severity and organ systems affected and in need of therapy.

EXPERIMENTAL PART

ISOLATION OF TRITERPENE SAPONINS FROM *MAESA BALANSAE*

The air-dried powdered leaves (3 kg) of *Maesa balansae* were extracted with chloroform to remove apolar material, and then with methanol:water (9:1). The alcoholic extract was evaporated under reduced pressure and the residue was partitioned between n-butanol (saturated with water) and water. The organic layer was evaporated to dryness and the residue was washed with acetone and filtered. The acetone insoluble part containing the saponins (10 g) was purified by reversed-phase HPLC (stationary phase RP-18 HS BDS Hyperprep 100 Å, 8 µm; 200 g, ø column 5 cm) with a gradient eluent system using:

A: 0,5% ammonium acetate in water,
B: methanol and
C: acetonitrile at a flow rate of 80 ml/min with UV-detection at 235 nm. Using the gradient eluent system (t=0 min) A:B:C (60:20:20) to (t=50 min) A:B:C (0:50:50) a pure saponin mixture (5 g) is obtained comprising six compounds.

Isolation of each of the six saponins was performed on the same column under the same conditions using the above described gradient solvent system. In order of elution, the following compounds were obtained:

Compound 1: MW=1532, $\lambda_{max}$=223.3 nm; was further purified using isocratic solvent system A:B:C (33:64:03); yield 230 mg.

Compound 2: MW=1510, $\lambda_{max}$=209.2 nm; gradient elution system: (t=0 min) A:B:C (42:29:29) to (t=end) A:B:C (24:38:38); yield 110 mg.

TABLE I

In vitro antileishmanial activity in primary mouse macrophages

| Leishmania species | | $EC_{50}$ (microgram/ml) | | | | |
|---|---|---|---|---|---|---|
| | | PX | meglumine | pentostam | ampho-B | itraconazole |
| Visceral | L. donovani | 0.05 | 12 | 6 | 0.1 | >12.5 |
| | L. infantum | 0.05 | 12 | 6 | 0.1 | >12.5 |
| Cutaneous | L. mexicana | 1 | >50 | 25 | 0.1 | nd |
| | L. major | 5 | >50 | >50 | 0.2 | nd |
| Mucocutaneous | L. panamensis | nd | nd | nd | nd | nd |
| | L. major | nd | nd | nd | nd | nd | nd: not done

Compound 3: MW=1532, $\lambda_{max}$=222.1 nm; isocratic solvent system: A:B:C (40:30:30); yield 1,000 mg.

Compound 4: MW=1510, $\lambda_{max}$=202.2 nm ;isocratic solvent system: A:B:C (59:00:41); yield 1,000 mg.

Compound 5: MW=1574, $\lambda_{max}$=203.4 nm; and isocratic solvent system: A:B:C (32:34:34); yield 220 mg.

Compound 6: MW=1552, $\lambda_{max}$=216.3 nm; isocratic solvent system: A:B:C (32:34:34) with recycling (4 times); yield 230 mg.

EVALUATION OF ANTILEISHMANIA ACTIVITY

The test drug PX used in the following examples comprises the mixture of saponins isolated from *Maesa balansae*.

1. In Vitro Antileishmanial Activity

Methods for the in vitro growth of Leishmania organisms and screening methodology are well documented in the international literature. Testing protocols are flexible and may be adapted according to the specific objectives and characteristics of the test compounds. Briefly, the following in vitro methodology has been used: Primary peritoneal macrophages derived from laboratory rodents or macrophage cell lines were seeded in multiwell tissue culture vessels and allowed to attach for about 24 hours. Amastigotes of the Leishmania species (obtained from target tissues of an infected donor animal or from amastigote-infected tissue cultures) or promastigotes of the Leishmania species were added at an appropriate infection ratio together with varying serially diluted concentrations of the drug or test compound. The test drug was solubilized in an appropriate solvent which was tolerated in the in vitro test system (DMSO ; water, alcohols, and the like work equally well) and added to the tissue culture medium. The cultures were incubated at 37° C. in 5% $CO_2$ for 5–15 days. Treatment of uninfected control cultures was also included in order to determine a selectivity index. Reference drug treated cultures were included as well so as to determine the relative potency of the test drug. Drug activity was determined in stained preparations as the percentage reduction of the total parasite load or the number of infected macrophages compared to the untreated control cultures. Reading was performed microscopically and $EC_{50}$-values (effective concentration for 50% inhibition) were determined. The percentage reduction and the $EC_{50}$-value serve as an indication for antileishmanial activity in vitro and provide significant leads for clinically useful agents.

2. In Vivo Antileishmanial Activity

Methods for in vivo maintenance of Leishmania organisms and animals models are well documented in the international literature. Balb-C mice and golden hamsters are the preferred laboratory animal species for primary isolation, maintenance and use in artificial infection models. Testing protocols are flexible and may be adapted according to the specific objectives and characteristics of the test compounds. Briefly, the following in vivo methodologies have been used:

For visceral Leishmania species: Balb-C mice or young hamsters were intravenously infected with about $10^6$ to $10^7$ amastigotes derived from the target organs (generally spleen) of an infected donor animal or from an in vitro culture of parasite forms. The animals were treated with the test compound at different dose levels (dose range: 0.1 to 80 mg/kg in 100% DMSO or any other acceptable vehicle), using different routes of administration and treatment schedules. Initiation of treatment was either at different times after infection (curatively), concomitant with infection (prophylactically) or before infection (residual activity). In the prophylactic study design, the first administration of the test drug is given immediately before or together with the artificial infection with the Leishmania species. In the curative study design, the first administration of the test drug is given several weeks after the artificial infection with the Leishmania species (early curative=when the first clinical signs appear; late curative=when the clinical symptoms are well established or become chronic). Drug activity was evaluated by determination of the total parasite burdens in the liver or any other relevant target tissue/organ, compared to the tissue/organ burdens in untreated control animals. The mean number of amastigotes is enumerated quantitatively or semi-quantitatively on stained impression smears or slides. The percentage reduction serves as an indication for antileishmanial activity and provides significant leads for clinically useful agents. The lowest active dose (LAD) is defined as the lowest dose which reduces the parasite burden in the primary target organ/tissue by at least 80%.

TABLE II

In vivo antileishmanial activity in mice and hamsters against visceral Leishmania species

| Animal species | dosing freq. | regimen timing | % reduction of parasite load in target organ after parenteral dosing at (mg/kg) | | | | | | | |
|---|---|---|---|---|---|---|---|---|---|---|
| | | | 40 | 20 | 10 | 5 | 2.5 | 1.25 | 0.63 | 0.32 |
| Mouse | 5× | proph. | 100 | 100 | 100 | 100 | 100 | 100 | 100 | 98 |
| | | cur. | 100 | 100 | 100 | 100 | 100 | | | |
| | 1× | proph. | 100 | 100 | 100 | 100 | 100 | | | |
| | | cur. | | | | 98 | 90 | 80 | | |
| Hamster | 5× | proph. | 100 | 100 | 100 | | | | | |
| | | cur. | | | | 100 | 100 | | | |
| | 1× | proph. | | | | 100 | 100 | 100 | | |
| | | cur. | | | | | | | | |

TABLE III

In vitro and in vivo activity against visceral *Leishmania infantum*

| | Activity against *L. infantum* | | |
|---|---|---|---|
| Product | in vitro IC50 (ng/ml) | in vivo LAD (mg/kg 1×) | Result Activity score |
| PX | 50 | 0.4 | +++ |
| compound-1 | 70 | 0.8 | ++ |
| compound-2 | 50 | >0.8 | ++ |
| compound-3 | 20 | 0.2 | +++ |
| compound-4 | 20 | 0.4 | +++ |
| compound-5 | 3400 | >0.8 | + |
| compound-6 | 700 | >0.8 | + |
| Tri-OH derivative | 10,000 | >40 | not active |
| Aglycon derivative | >50,000 | >40 | not active |

For cutaneous and mucocutaneous Leishmania species: Balb-C mice or young hamsters were infected intradermally or subcutaneously with about $10^6$ to $10^7$ amastigotes derived from the target organs (generally skin lesion) of an infected donor animal or from an in vitro culture of parasite forms. The animals were treated with the test compound at different dose levels (mg/kg in 100% DMSO or any other acceptable vehicle), using different routes of administration and treatment schedules. Initiation of treatment was either before infection (prophylactically) or at different times after infection (curatively). In the prophylactic study design, the first administration of the test drug is given immediately before or together with the artificial infection with the Leishmania species. In the curative study design, the first administration of the test drug is given several weeks after the artificial infection with the Leishmania species (early curative=when the first dermal lesions appear; late curative=when dermal lesions are well established or become chronic). Drug activity was evaluated either by determination of the severity of the lesion in the relevant target tissue/organ (primary parameter) or of the parasite burdens in the relevant target tissue/organ (secondary parameter), compared to untreated control animals. The lesion size was assessed quantitatively using the method of J. El-On. and A. D. Hamburger [Trans. Roy. Soc. Trop. Med. Hyg., 81, 734–737 (1987)]. The percentage reduction serves as an indication for antileishmanial activity and provides significant leads for clinically useful agents. The lowest active dose (LAD) is defined as the lowest dose which prevents lesions to develop, stops further evolution of the lesions or induces a clinical cure of the lesions in the primary target organ or tissue.

TABLE IV

In vivo antileishmanial activity in mice and hamsters against cutaneous and mucocutaneous Leishmania species A. Prophylactic treatment
In the prophylactic study design, the first administration of the test drug is given immediately before the artificial infection with the Leishmania species

| *L. mexicana* (proph.) | skin lesion size* at weeks post infection | | | | | | | | | | | | |
|---|---|---|---|---|---|---|---|---|---|---|---|---|---|
| Group | 0 | 1 | 2 | 3 | 4 | 5 | 6 | 7 | 8 | 9 | 10 | 11 | 12 |
| Untreated control | 0 | 0 | 0 | 0 | 0 | 1 | 1 | 10 | 33 | 59 | 86 | 108 | 98 |
| Ampho-B 10 mg/kg | 0 | 0 | 0 | 0 | 0 | 1 | 2 | 7 | 13 | 34 | 85 | 101 | 112 |
| Pentostam 250 mg/kg | 0 | 0 | 0 | 0 | 0 | 0 | 1 | 9 | 13 | 22 | 37 | 50 | 51 |
| PX 10 mg/kg | 0 | 0 | 0 | 0 | 0 | 0 | 0 | 0 | 0 | 0 | 0 | 0 | 0 |
| PX 5 mg/kg | 0 | 0 | 0 | 0 | 0 | 0 | 0 | 0 | 0 | 0 | 0 | 0 | 0 |
| PX 2.5 mg/kg | 0 | 0 | 0 | 0 | 0 | 0 | 0 | 0 | 0 | 0 | 0 | 0 | 0 |

| *L. major* (proph.) | skin lesion size* at weeks post infection | | | | | | | | |
|---|---|---|---|---|---|---|---|---|---|
| Group | 0 | 1 | 2 | 3 | 4 | 5 | 6 | 7 | 8 |
| Untreated control | 0 | 0 | 1 | 1 | 17 | 20 | 27 | 72 | 113 |
| Ampho-B 10 mg/kg | 0 | 0 | 1 | 1 | 12 | 31 | 41 | 57 | 95 |
| Pentostam 250 mg/kg | 0 | 0 | 1 | 1 | 7 | 16 | 20 | 32 | 60 |

TABLE IV-continued

In vivo antileishmanial activity in mice and hamsters
against cutaneous and mucocutaneous Leishmania species

| | | | | | | | | | | |
|---|---|---|---|---|---|---|---|---|---|---|
| PX 10 mg/kg | 0 | 0 | 0 | 0 | 0 | 0 | 0 | 0 | 0 | |
| PX 5 mg/kg | 0 | 0 | 0 | 0 | 0 | 0 | 0 | 0 | 0 | |
| PX 2.5 mg/kg | 0 | 0 | 0 | 0 | 0 | 0 | 0 | 0 | 0 | |

| L. panamensis (proph.) | skin lesion size* at weeks post infection | | | | | | | | | | | | |
|---|---|---|---|---|---|---|---|---|---|---|---|---|---|
| Group | 0 | 1 | 2 | 3 | 4 | 5 | 6 | 7 | 8 | 9 | 10 | 11 | 12 |
| Untreated control | 0 | 0 | 0 | 0 | 1 | 6 | 30 | 42 | 49 | 58 | 55 | 67 | 56 |
| Ampho-B 10 mg/kg | 0 | 0 | 0 | 0 | 1 | 9 | 15 | 30 | 30 | 42 | 42 | 43 | 39 |
| Pentostam 250 mg/kg | 0 | 0 | 0 | 0 | 0 | 0 | 0 | 0 | 0 | 0 | 0 | 0 | 0 |
| PX 10 mg/kg | 0 | 0 | 0 | 0 | 0 | 0 | 0 | 0 | 0 | 0 | 0 | 0 | 0 |
| PX 5 mg/kg | 0 | 0 | 0 | 0 | 0 | 0 | 0 | 0 | 0 | 0 | 0 | 0 | 0 |
| PX 2.5 mg/kg | 0 | 0 | 0 | 0 | 0 | 0 | 0 | 0 | 0 | 0 | 0 | 0 | 0 |

B. Curative treatment
In the curative study deign, the first administration of the test drug
is given several weeks after the artificial infection with the Leishmania species
(generally when the first clinical signs appear).

| L. mexicana (cur) | Dose | freq./ | skin lesion size* at weeks post infection | | | | |
|---|---|---|---|---|---|---|---|
| Group | mg/kg | week | 5** | 6 | 7 | 8 | 9 |
| Untreated control | | | 1.7 | 3.6 | 10.7 | 17.7 | 32.8 |
| Pentostam | 250 | 2× | 2.5 | 4.9 | 8.5 | 13.3 | 19.2 |
| PX | 1 | 1× | 1.8 | 3.6 | 4.2 | 3.1 | 2.2 |
| PX | 1 | 2× | 2.2 | 3.7 | 3.6 | 2.4 | 2.3 |
| PX | 2 | 1× | 1.6 | 2.6 | 1.3 | 1.3 | 1.4 |
| PX | 2 | 2× | 1.3 | 1.1 | 1.8 | 0.7 | 0.6 |

| L. major (cur) | Dose | freq./ | skin lesion size* at weeks post infection | | | | | | |
|---|---|---|---|---|---|---|---|---|---|
| Group | mg/kg | week | 2** | 3 | 4 | 5 | 6 | 7 | 8 | 9 |
| Untreated control | | | 1 | 14 | 32 | 42 | 50 | 59 | 64 | 148 |
| Pentostam | 250 | 2× | 1 | 13 | 24 | 33 | 36 | 42 | 48 | 123 |
| PX | 1 | 1× | 1 | 14 | 27 | 34 | 40 | 46 | 59 | 64 |
| PX | 1 | 2× | 1 | 12 | 19 | 27 | 32 | 33 | 32 | 33 |
| PX | 2 | 1× | 1 | 16 | 25 | 30 | 33 | 38 | 42 | 42 |
| PX | 2 | 2× | 1 | 9 | 23 | 29 | 30 | 28 | 32 | 35 |

| L. panamensis (cur) | Dose | freq./ | skin lesion size* at weeks post infection | | | | |
|---|---|---|---|---|---|---|---|
| Group | mg/kg | week | 5** | 6 | 7 | 8 | 9 |
| Untreated control | | | 2.8 | 8.5 | 20.8 | 30.5 | |
| Pentostam | 250 | 2× | 2.3 | 1.2 | 0.5 | 0.1 | |
| PX | 1 | 1× | 2.2 | 2.1 | 3.5 | 3.7 | |
| PX | 1 | 2× | 1.2 | 1.8 | 2.8 | 1.2 | |
| PX | 2 | 1× | 1.9 | 4.0 | 4.8 | 2.6 | |
| PX | 2 | 2× | 2.9 | 1.6 | 2.3 | 1.7 | |

*using the formula: [vertical diameter × horizontal diameter]/2 (mm$^2$)
**initiation of treatment

TABLE V

In vivo antileishmanial activity of the PX mixture against different Leishmania species Lowest active dose (LAD) regimen in Balb-C mice*

| Model | PX | Sodium stibogluconate Pentostam ® | Amphothericin-B Fungizone ® |
|---|---|---|---|
| L. donovani | | | |
| prophylactic | 0.4 mg/kg, 1× | 250 mg/kg, 1× | not effective |
| curative early | 1.6 mg/kg, 1× | 250 mg/kg, 1× | not effective |

TABLE V-continued

In vivo antileishmanial activity of the PX mixture against different Leishmania species

| | Lowest active dose (LAD) regimen in Balb-C mice* | | |
|---|---|---|---|
| Model | PX | Sodium stibogluconate Pentostam ® | Amphothericin-B Fungizone ® |
| curative late | nd | nd | nd |
| residual activity | 5 days after single 2.5 mg/kg dose | nd | not effective |
| *L mexicana* | | | |
| prophylactic | <0.5 mg/kg, 6× (alternate days) | >>250 mg/kg, 6× (alternate days) | not effective |
| curative early | <1 mg/kg, 4× (in 4 weeks) | >>250 mg/kg, 8× (in 4 weeks) | nd |
| curative late | <1 mg/kg, 2×/w for 4 weeks | nd | nd |
| *L. panamensis* | | | |
| prophylactic | <0.5 mg/kg, 6× (alternate days) | <250 mg/kg, 6× (alternate days) | not effective |
| curative early | 1 mg/kg, 4× (in 4 weeks) | <250 mg/kg, 8× (in 4 weeks) | nd |
| curative late | <1 mg/kg, 2×/w for 4 weeks | nd | nd |
| *L. major* | | | |
| prophylactic | 2 mg/kg, 6× (alternate days) | >>250 mg/kg, 6× (alternate days) | not effective |
| curative early | 1 mg/kg, 4× (in 4 weeks) | >>250 mg/kg, 8× (in 4 weeks) | nd |
| curative late | 1 mg/kg, 22× (in 11 weeks) | nd | nd |

*based on amastigote burdens in the liver for visceral forms and on lesion size for cutaneous forms

What is claimed is:

1. A triterpene saponin having the, formula

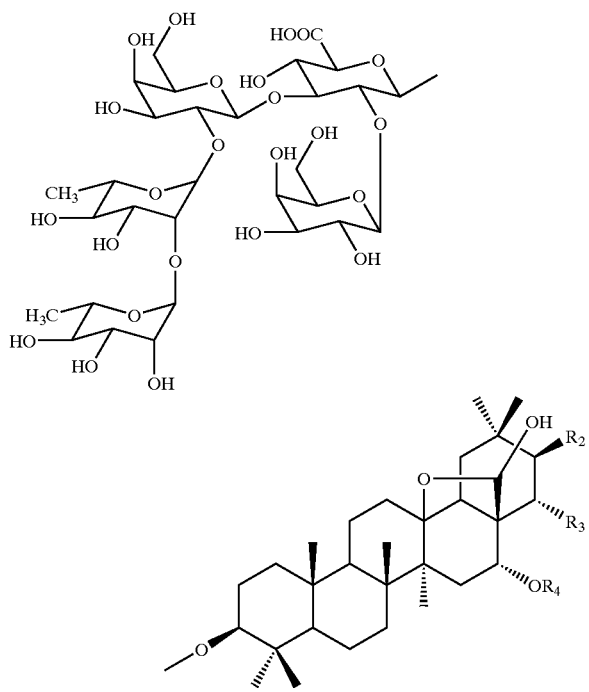

wherein $R_2$ is —O(C=O)$C_6H_5$ or —O(C=O)C($CH_3$)=CH$CH_3$,
$R_3$ is (E) or (Z) —O(C=O)CH=CH—$C_6H_5$, and
$R_4$ is hydrogen or —(C=O)$CH_3$.

2. A compound according to claim 1 wherein
in compound 1, $R_2$ is —O(C=O)$C_6H_5$,
$R_3$ is (Z) —O(C=O)CH=CH—$C_6H_5$,
$R_4$ is hydrogen;
in compound 2, $R_2$ is —O(C=O)C($CH_3$)=CH$CH_3$,
$R_3$ is (Z) —O(C=O)CH=CH—$C_6H_5$,
$R_4$ is hydrogen;
in compound 3, $R_2$ is —O(C=O)$C_6H_5$,
$R_3$ is (E) —O(C=O)CH=CH—$C_6H_5$,
$R_4$ is hydrogen;
in compound 4, $R_2$ is —O(C=O)C($CH_3$)=CH$CH_3$,
$R_3$ is (E) —O(C=O)CH=CH—$C_6H_5$,
$R_4$ is hydrogen;
in compound 5, $R_2$ is —O(C=O)$C_6H_5$,
$R_3$ is (E) —O(C=O)CH=CH—$C_6H_5$,
$R_4$ is —(C=O)$CH_3$; or
in compound 6, $R_2$ is —O(C=O)C($CH_3$)=CH$CH_3$,
$R_3$ is (E) —O(C=O)CH=CH—$C_6H_5$,
$R_4$ is —(C=O)$CH_3$.

3. A composition according to claim 1 adapted for parenteral administration.

4. A pharmaceutical composition comprising a pharmaceutically acceptable excipient and as an active ingredient a triterpene saponin as defined in claim 1.

* * * * *